United States Patent [19]

Cross et al.

[11] 3,954,441

[45] May 4, 1976

[54] (ALKYNYLOXY)ALKYL AND (ALKENYLOXY)ALKYL CARBAMATES AND THEIR USE AS HERBICIDES

[75] Inventors: Barrington Cross, Rocky Hill; Charles Paul Grasso, Cranbury, both of N.J.

[73] Assignee: American Cyanamid Company, Stamford, Conn.

[22] Filed: Oct. 15, 1974

[21] Appl. No.: 514,858

Related U.S. Application Data

[62] Division of Ser. No. 344,667, March 26, 1973, Pat. No. 3,867,429.

[52] U.S. Cl. .................................. 71/106; 71/100
[51] Int. Cl.$^2$ ............................................ A01N 9/24
[58] Field of Search ............................. 71/106, 120

[56] References Cited

UNITED STATES PATENTS

| | | | |
|---|---|---|---|
| 3,277,141 | 10/1966 | Steinbrunn et al. | 71/120 |
| 3,434,822 | 3/1969 | Wilson et al. | 71/106 |
| 3,865,867 | 2/1975 | Olin et al. | 71/106 |

FOREIGN PATENTS OR APPLICATIONS

| | | | |
|---|---|---|---|
| 742,291 | 1/1970 | Belgium | 71/106 |

Primary Examiner—Glennon H. Hollrah
Attorney, Agent, or Firm—H. G. Jackson

[57] ABSTRACT

This invention is novel (alkynyloxy)alkyl and (alkenyloxy)alkyl carbamates, which are highly effective herbicidal agents.

12 Claims, No Drawings

(ALKYNYLOXY)ALKYL AND (ALKENYLOXY)ALKYL CARBAMATES AND THEIR USE AS HERBICIDES

This is a division of application Ser. No. 344,667, filed Mar. 26, 1973, now U.S. Pat. No. 3,867,429.

BACKGROUND OF THE INVENTION

1. Field of the Invention

The invention pertains to novel organic chemicals useful as herbicides.

2. Description of the Prior Art m-Ureidophenyl carbamates are described as herbicidal agents in U.S. Pat. No. 3,434,822 (1969). Similarly, alkoxyalkylcarbamoyloxy phenylureas are described as herbicidal agents in Belgium Pat. No. 742,291, issued Jan. 30, 1970. The compounds described in these patents are shown to be quite effective as preemergence and postemergence herbicidal agents against certain species of undesirable plants when applied at rates between 1.5 pounds and 6 pounds per acre. However, it can also be seen that the activity of the described compounds are generally non-selective and are not recommended for use in the presence of economically important crops, such as corn, cotton, soybeans or sorghum.

It would, therefore, be advantageous if more effective compounds could be found which would provide better control of undesirable plants at even lower rates of application. Surprisingly, we have found that the compounds of our invention are highly effective herbicidal agents when applied at rates as low as 0.06 pound per acre. We have also discovered that the compounds can be used for selective control of undesirable plants in the presence of several agronomic crops, such as corn, cotton, soybeans or sorghum.

SUMMARY

This invention is novel (alkynyloxy)alkyl and (alkenyloxy)alkyl carbamates represented by the structure:

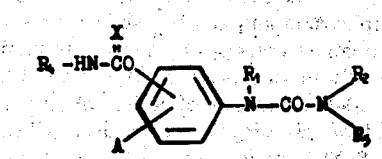

wherein $R_1$ is hydrogen, hydroxyl or alkyl $C_1$–$C_4$; $R_2$ is hydrogen, alkyl $C_1$–$C_4$ or alkoxy $C_1$–$C_4$; $R_3$ is hydrogen, alkyl, $C_1$–$C_4$, alkoxy $C_1$–$C_4$,

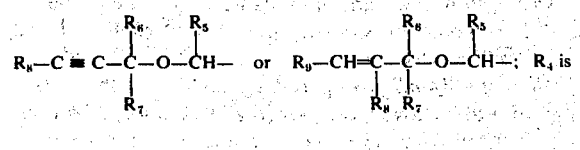

$R_5$ is hydrogen or n-alkyl $C_1$–$C_4$; $R_6$ and $R_7$ are hydrogen or alkyl $C_1$–$C_4$; $R_8$ and $R_9$ are hydrogen, alkyl $C_1$–$C_4$ or halogen, preferably chlorine, bromine or iodine; X is sulfur or oxygen; and A is hydrogen, halogen (preferably chlorine or bromine) or alkyl $C_1$–$C_4$; provided that A and —O—CX—NHR$_4$ are meta- and para-, respectively, or or para- and meta-, respectively; and further provided that $R_2$ is hydrogen when $R_3$ is either

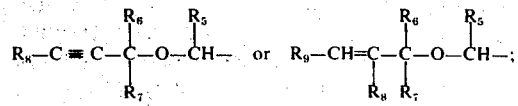

and a process for the compound manufacture.

Preferred compounds are those having the above formula, wherein $R_1$ is hydrogen; $R_2$ is methyl or methoxy; $R_3$ is methyl; A is hydrogen; X is oxygen; $R_4$ NHCX—O— is meta- to the ureido group; $R_4$, $R_6$, $R_7$, $R_8$ and $R_9$ are as previously described, and $R_5$ is hydrogen.

This invention includes novel herbicidal compositions and methods for the preemergence of postemergence control of undesirable plant species with the above-identified compounds and/or compositions. Further, the invention includes methods for the selective preemergence and selective postemergence control of undesirable plant species in the presence of seeded or growing crops.

DETAILED DESCRIPTION

In accordance with the invention, (alkynyloxy)alkyl carbamates and (alkenyloxy)alkyl carbamates, illustrated by the formula given above, are prepared by the interaction of an (alkynyloxy)alkyl isocyanate, (alkynyloxy)alkyl isothiocyanate, (alkenyloxy)alkyl isocyanate or (alkenyloxy)alkyl isothiocyanate on an appropriately substituted hydroxyphenyl urea (II) in the presence of a base in an organic solvent as shown below:

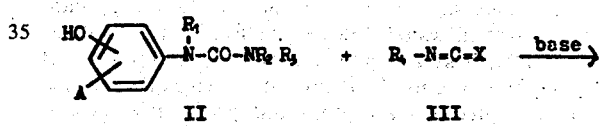

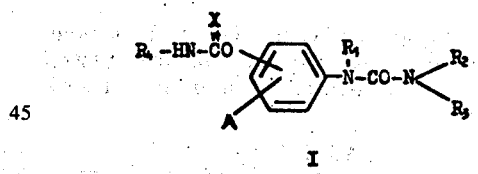

wherein $R_1$, $R_2$, $R_3$, $R_4$, X and A represent the members described above.

In order to obtain the carbamates of the invention, the reaction conditions must be chosen carefully. The

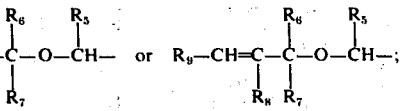

phenol (II) can be either suspended or dissolved in an organic solvent, though complete solution results in higher yields. Tetrahydrofuran is an excellent solvent for the reaction, but many of the phenols react equally well in other solvents, such as diethyl ether, p-dioxane, dimethylformamide, acetone, ethyl acetate, methyl isobutyl ketone, benzene and the like. Addition of a base or catalyst to the reaction mixture is also beneficial. This is demonstrated by the fact that improved product yields are obtained with the addition, to the reaction mixture, of a catalyst, such as dibutyltin diacetate or a molar equivalent or excess of base. Triethylamine, pyridine, triisopropylamine and quinoline are typical of the bases which may be employed.

The isocyanates or isothiocyanates (III) are generated, preferably in ethereal solution (e.g. diethyl ether or tetrahydrofuran), but are not isolated, at about 0°C. to 20°C. by the action of silver cyanate or silver thiocyanate upon the appropriate chloromethyl ether. The reaction may be graphically illustrated as follows:

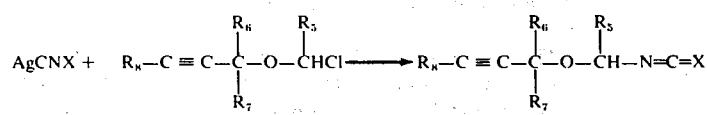

where $R_5$, $R_6$, $R_7$, $R_8$ X are as described above, or

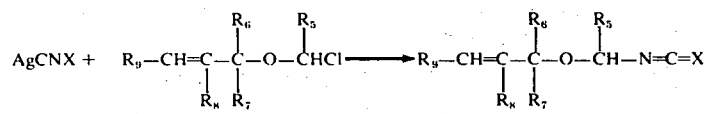

wherein $R_5$, $R_6$, $R_7$, $R_8$, $R_9$ and X are as described above.

Other procedures may also be employed to generate the isocyanates or isothiocyanates (III), e.g. other metal cyanates using a variety of solvent conditions (e.g. sodium cyanate-acetonitrile-benzene) may be used.

The cooled generated isocyanate or isothiocyanate solution is then added slowly to a stirred solution of the phenol (II), base and solvent. After the addition and stirring, the solution is evaporated, washed with 1% ice-cold aqueous alkali solution, preferably sodium hydroxide, water washed and treated with an organic solvent, either to give a final wash, or to crystallized the product.

Examples of the ureido phenols (II) used in the preparation of the (alkynyloxy)alkyl and (alkenyloxy)alkyl carbamates (I) of the present invention are set forth below in Table I.

TABLE I

Ureidophenols

| Number | $R_1$ | $R_2$ | $R_3$ | A | OH |
|---|---|---|---|---|---|
| 1 | H | H | $OCH_3$ | 4-H | 3 |
| 2 | H | H | $CH_3$ | 4-H | 3 |
| 3 | H | $CH_3$ | $CH_3$ | 4-H | 3 |
| 4 | H | $CH_3$ | $OCH_3$ | 4-H | 3 |
| 5 | H | H | $C_2H_5$ | 4-H | 3 |
| 6 | H | H | $C_3H_7$-n | 4-H | 3 |
| 7 | H | H | $C_4H_9$-n | 4-H | 3 |
| 8 | H | H | $C_4H_9$-t | 4-H | 3 |
| 9 | H | H | $CH_2-C\equiv CH$ | 4-H | 3 |
| 10 | $CH_3$ | $CH_3$ | $CH_3$ | 4-H | 3 |
| 11 | H | $CH_3$ | $CH_3$ | 4-Cl | 3 |
| 12 | H | $CH_3$ | $OCH_3$ | 4-Cl | 3 |
| 13 | H | $CH_3$ | $CH_3$ | 3-H | 4 |
| 14 | H | $CH_3$ | $CH_3$ | 3-Cl | 4 |
| 15 | H | $CH_3$ | $OCH_3$ | 3-Cl | 4 |
| 16 | H | H | $CH_2-CH=CH_2$ | 4-H | 3 |

Numbers 2, 5 through 9 and 16 were prepared by the reaction of the appropriate isocyanate with the appropriately substituted-aminophenol in an aprotic solvent in the absence of base or acid catalysis.

Examples of the isocyanates and isothiocyanates (III) generated include, but are not limited to, those set forth in Table II below.

TABLE II

| | Isocyanates and Isothiocyanates $R_4N=C=X$ | |
|---|---|---|
| Number | $R_4$ | X |
| 1 | $HC\equiv C-CH_2-O-CH_2-$ | O |
| 2 | $HC\equiv C-CH_2-O-CH(CH_3)-$ | O |
| 3 | $HC\equiv C-CH(CH_3)-O-CH_2-$ | O |
| 4 | $HC\equiv C-CH(CH_3)-O-CH(CH_3)-$ | O |
| 5 | $HC\equiv C-C(CH_3)_2-O-CH_2-$ | O |
| 6 | $HC\equiv C-C(CH_3)_2-O-CH(CH_3)-$ | O |
| 7 | $Cl-C\equiv C-C(CH_3)_2-O-CH_2-$ | O |
| 8 | $CH_3-C\equiv C-C(CH_3)_2-O-CH_2-$ | O |
| 9 | $CH_2=CH-CH_2-O-CH_2-$ | O |
| 10 | $CH_2=C(Cl)CH_2-O-CH_2-$ | O |
| 11 | $CHCl=CH-CH_2-O-CH_2-$ | O |
| 12 | $CH_2=C(CH_3)-CH_2-O-CH_2-$ | O |
| 13 | $CH_2=CH-CH(CH_3)-O-CH_2-$ | O |
| 14 | $CH_2=CH-C(CH_3)_2-O-CH_2-$ | O |
| 15 | $HC\equiv C-C(CH_3)_2-O-CH_2-$ | S |
| 16 | $HC\equiv C-CH_2-O-CH_2-$ | S |
| 17 | $CH_2=CH-CH_2-O-CH_2-$ | S |

The compounds of the invention are highly effective herbicidal agents. They provide selective control of a wide variety of broadleaf weeds and grasses at very low rates of application and can be used for preemergence or postemergence control of undesirable plants. They can be used alone or in combination with other herbicides and are particularly effective when utilized for the control of undesirable weeds and grasses in the presence of agronomic crops, such as corn, cotton, soybeans and sorghum.

The active compounds can be prepared as liquid or solid formulations and applied as such to the foliage of undesirable plants or to soil containing seeds of undesirable plants.

Among the solid formulations which can be prepared are dusts, dust concentrates, wettable powders and granular formulations.

Dusts are usually prepared by dissolving the active ingredient in a lower alcohol (e.g. methanol, isopropanol or butanol) or a ketone (e.g. acetone, methylethylketone or cyclohexanone) and spraying the thus-prepared solution on a finely divided carrier, such as attapulgite, kaolin, diatomaceous earth, or silica. Dusts usually contain about 1% to 15% by weight of the active compound.

Dust concentrates are generally prepared in the same manner as dusts excepting that about 16% to about 75% by weight of the active compound is applied to or mixed with the carrier.

Wettable powders are made up in the same manner as the dust concentrates, excepting that about 1% to 5% by weight of a surfactant and about 1% to 5% by weight of a dispersant are added to the formulation. In practice, the wettable powders are generally dispersed in water or other suitable liquid and applied to the soil or foliage as a dilute spray.

Surfactants which may be used in preparation of the wettable powders are naphthalene sulfonic acid condensate, polyoxyethylate vegetable oil, Sorbitan monooleate, mono- and diglycerides of fatty acids, alkyl phenoxy polyoxyethylene ethanol and sodium alkyl naphthalene sulfonate. The monocalcium salt of a polymerized alkyl aryl sulfonic acid and sodium lignin sulfonate are representative of dispersants which can be used in the wettable powder formulations.

Granular formulations can be prepared by applying an alcoholic or ketonic solution of the active material to a granular sorptive carrier, such as attapulgite, kaolin, activated carbon or corn cob grits. Non-sorptive carriers, such as granular limestone, walnut shell, coconut shell or sand may be used in the preparation of granular formulations by (1) wetting the granules with a binder solution (e.g. sodium lignosulfonate) or an alcoholic or ketonic solution of the active ingredient, and (2) coating the wetted particles with a dust or dust concentrate containing the active compound or with an inert dusting agent, such as talc or clay.

Emulsifiable concentrates can be prepared by dissolving about 25% to 75% by weight of the active compound in a lower alcohol or ketone, as mentioned above, and admixing therewith from about 1% to 10% by weight of an emulsifier. For use in the field, the concentrate is usually dispersed in water or other suitable diluent and applied as a liquid spray.

Effective control of a wide variety of broadleaf weeds and grasses is usually obtained by application of a sufficient amount of the formulated composition to provide about 0.06 pound per acre to 8 pounds per acre of active compound. Selective control of said weeds and grasses, on the other hand, generally requires only about 0.06 pound per acre to about 2 pounds per acre of the active compound.

This invention is further illustrated by the following examples which are not to be construed as limitative.

EXAMPLE 1

Preparation of Chloromethyl 1,1-dimethyl-2-propynyl ether

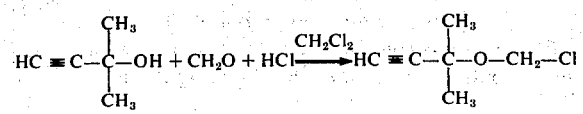

Hydrogen chloride gas (80 grams, 2.2 moles) is bubbled into a mixture of paraformaldehyde (60.2 grams, 2.0 moles), and 2-methyl-3-butyne-2-ol (168.2 grams, 2.0 moles) in methylene chloride (500 ml.) over a 25 minute period, with constant stirring while the temperature is maintained between 2°C. to 8°C. Upon completion of the addition, the reaction temperature is allowed to rise to 10°C.; then the lower organic phase is separated, washed with ice water, separated, and dried over anhydrous calcium chloride for 18 hours. The methylene chloride is removed by evaporation, and the resulting liquid distilled at reduced pressure to give a forerun of 10 grams, boiling point 55°C. to 57°C./54 mm. and the major fraction as the chloromethyl ether, chloromethyl 1,1-dimethyl-2-propynyl ether, 140 grams, 53% boiling point 54°C. to 58°C./37 mm. to 40 mm.

The same chloromethyl ether was also prepared in the absence of an added solvent in 32% yield, boiling point 39.5°C. to 41.5°C./16 mm. to 17 mm.

EXAMPLE 2

Preparation of Chloromethyl 1-methyl-2-propynyl ether

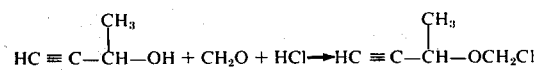

Hydrogen chloride gas is bubbled into a suspension of paraformaldehyde (30.1 grams, 1 mole) in 3-butyne-2-ol (70.1 grams, 1 mole), with constant stirring, at −30°C. The exotherm is controlled between −15°C. and 5°C., and the hydrogen chloride addition continued until the solid dissolves. Upon completion of the addition, the reaction is allowed to attain 15°C. and sodium chloride added to aid the separation of the organic layer. The upper organic layer is separated and dried over anhydrous calcium chloride for 3 hours and distilled under reduced pressure to give a forerun of 3 ml., boiling point 22°C. to 36°C./35 mm. to 32 mm. and a major fraction 83 grams, 70%, boiling point 36°C. to 39°C./32 mm. as the product chloromethyl 1-methyl-2-propynyl ether.

EXAMPLE 3

Preparation of 1-Chloroethyl 1,1-dimethyl-2-propynyl ether

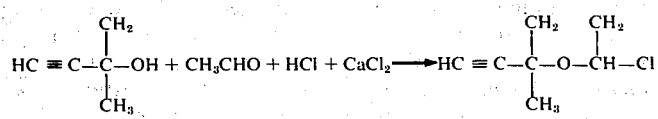

Hydrogen chloride gas (50 grams) is bubbled into a cooled, well-stirred solution at −25°C. to −15°C. of 2-methyl-3-butyne-2-ol (84.1 grams, 1 mole) and acetaldehyde (44.05 grams, 1 mole) in dry methylene chloride (500 ml.) containing a suspension of anhydrous calcium chloride (222 grams, 2 moles). After the addition is complete, the reaction mixture temperature is allowed to attain 5°C. to 10°C. for 30 minutes, and then is filtered and the filtrate concentrated to a volume of 240 ml. A 160 ml. portion is distilled under reduced pressure through a short column to give a forefun followed by the product 1-chloroethyl 1,1-dimethyl-2-propynyl ether as a colorless liquid, 44.6 grams, 46% boiling point 88°C. to 92°C./55 mm. This product is extremely sensitive to air or moisture, fuming instantly.

EXAMPLE 4

Preparation of 1-Chloroethyl 1-methyl-2-propynyl ether

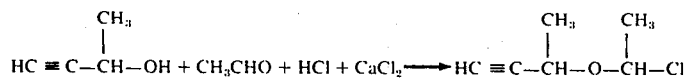

Hydrogen chloride gas (25 grams) is bubbled for ½ hour into a cooled, well-stirred solution at −25°C. to −10°C. of 3-butyne-2-ol (33.2 grams, 0.473 mole) and acetaldehyde (20.8 grams, 0.473 mole) in dry methylene chloride (200 ml.) containing a suspension of calcium chloride (111 grams, 1 mole). After the addition is complete, the reaction mixture is allowed to attain 5°C. to 10°C. over a 1 hour period; then the mixture is filtered, redried over anhydrous calcium chloride (50 grams), and set aside overnight. After filtration, the filtrate is concentrated on a rotary evaporator, and the residual liquid distilled under reduced pressure through a short column to give a 5 ml. forerun, followed by the product 1-chloroethyl 1-methyl-2-propynyl ether, boiling point 68°C. to 70°C./111 mm. to 115 mm., 35 grams (56.3%). This product is extremely sensitive to moisture, fuming instantly.

EXAMPLE 5

Preparation of 1-Chloroethyl 2-propynyl ether

1-Chloroethyl 2-propynyl ether

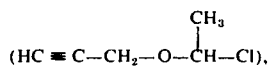

boiling point 57°C. to 63°C./57 mm. to 60 mm. was prepared in 47% yield by a procedure similar to Example 4. Similarly, the alkenyl ethers corresponding to the compounds of Examples 1 through 5 can be prepared by substituting the appropriate alkenyl alcohol for the alkynyl alcohol referred to in the Examples 1 through 5.

EXAMPLE 6

Preparation of m-(3-Methoxy-3-methylureido)phenyl [(1,1-dimethyl-2-propynyloxy)methyl]carbamate

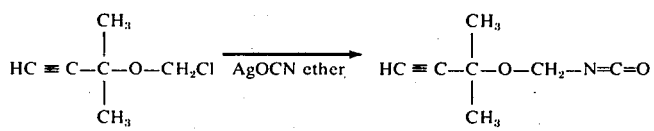

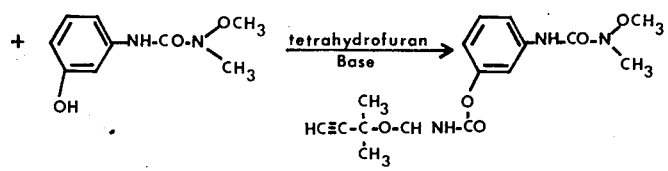

1,1-Dimethyl-2-propynyl chloromethyl ether (4 grams, 0.03 mole) is added dropwise with stirring at 0°C. to 5°C. to a dry ether (75 ml.) suspension of silver cyanate (4.5 grams, 0.03 mole). After stirring for 1 hour at 0°C. to 10°C., then a further hour at 23°C., the mixture is filtered to give a solutin containing the generated isocyanate. (Infrared spectrum of the solution showed intense absorption at ·γ2240 cm.$^{-1}$, i.e. N—C—O).

The ethereal isocyanate solution is added dropwise to a dry tetrahydrofuran (20 ml.) solution of 1-(m-hydroxyphenyl)-3-methoxy-3-methylurea (5.88 grams, 0.03 mole) containing triethylamine (3.34 grams, 0.031 mole) at 23°C. The addition is slightly exothermic, and the temperature rises to 27°C. After stirring for 45 minutes, a solid separates and the mixture is filtered, and the filtrate evaporated to an oil which is dissolved in chloroform. Extraction of this layer with aqueous sodium hydroxide 1%, and acidification of this layer, gives recovered ureidophenol, 1.5 grams. The solid, filtered from the reaction, is water washed and dried to give 4.34 grams, 58%, melting point 121°C. to 122°C.

An analytical sample has melting point 121°C. to 122°C. prepared by crystallization from benzene-n-hexane.

Analysis Calcd. for $C_{16}H_{21}N_3O_5$: C, 57.30; H, 6.31; N, 12.53. Found: C, 57.45; H, 6.44; N, 12.59.

Following the above procedure yields the compounds set forth in Tables III and IV below.

TABLE III

(Alkynyloxy)alkyl and (Alkenyloxy)alkyl Carbamates

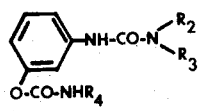

| $R_2$ | $R_3$ | $R_4$ | Melting Point °C. | % Yield (Crystallized) | Solvent of Crystallization | Analyses Calculated | Found |
|---|---|---|---|---|---|---|---|
| CH$_3$ | CH$_3$ | —CH$_2$—O—CH$_2$—CH=CH$_2$ | 133–134 | 12.3 | Benzene | C, 57.32<br>H, 6.53<br>N, 14.35 | 57.06<br>6.47<br>14.16 |
| CH$_3$ | OCH$_3$ | —CH$_2$—O—CH$_2$—CH=CH$_2$ | 113.5–114.5 | 28.0 | Benzene-Hexane | C, 54.36<br>H, 6.14<br>N, 13.59 | 54.16<br>6.31<br>13.73 |
| CH$_3$ | CH$_3$ | —CH$_2$—O—CH$_2$—C≡CH | 149–150 | 5.0 | Benzene | C, 57.72<br>H, 5.88<br>N, 14.43 | 57.28<br>5.84<br>14.23 |
| CH$_3$ | CH$_3$ | —CH$_2$—O—CH(CH$_3$)—C≡CH | 150–151.5 | 17.0 | Benzene-Ethyl acetate | C, 59.00<br>H, 6.27<br>N, 13.76 | 58.69<br>6.29<br>13.65 |
| CH$_3$ | CH$_3$ | —CH$_2$—O—C(CH$_3$)$_2$—C≡CH | 144–146 | 13.6 | Benzene-Ethyl acetate | C, 60.17<br>H, 6.63<br>N, 13.16 | 60.14<br>6.63<br>12.94 |
| CH$_3$ | OCH$_3$ | —CH$_2$—O—CH$_2$—C≡CH | 126–127 | 13.0 | Benzene-Hexane | C, 54.72<br>H, 5.58<br>N, 13.41 | 54.84<br>5.52<br>13.41 |
| CH$_3$ | OCH$_3$ | —CH$_2$—O—CH(CH$_3$)—C≡CH | 133–134 | 22.0 | Benzene-Hexane | C, 56.06<br>H, 5.96<br>N, 13.08 | 56.16<br>6.00<br>13.04 |
| CH$_3$ | OCH$_3$ | —CH(CH$_3$)—O—C(CH$_3$)$_2$—C≡CH | 104–106 | 27.0 | Benzene-Hexane | C, 58.44<br>H, 6.64<br>N, 12.03 | 58.41<br>6.73<br>12.03 |
| CH$_3$ | OCH$_3$ | —CH(CH$_3$)—O—CH$_2$—C≡CH | 110–111 | 32.0 | Benzene-Hexane | C, 56.06<br>H, 5.96<br>N, 13.08 | 56.54<br>6.00<br>12.71 |
| CH$_3$ | OCH$_3$ | —CH(CH$_3$)—O—CH(CH$_3$)—C≡CH | 90–92 | 25.0 | Benzene-Hexane | C, 57.30<br>H, 6.31<br>N, 12.53 | 58.04<br>6.48<br>12.25 |
| H | CH$_3$ | —CH$_2$—O—C(CH$_3$)$_2$—C≡CH | 88–90 | 28.0 | — | C, 59.00<br>H, 6.27<br>N, 13.26 | 59.01<br>6.45<br>13.97 |

TABLE IV

(Alkynyloxy)alkyl and (Alkenyloxy)alkyl Carbamates

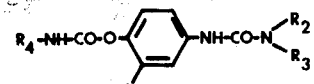

| $R_2$ | $R_3$ | $R_4$ | A | Melting Point °C. | % Yield (Crystallized) | Solvent of Crystallization | Analyses Calculated | Found |
|---|---|---|---|---|---|---|---|---|
| CH$_3$ | CH$_3$ | —CH$_2$—O—C(CH$_3$)$_2$—C≡CH | Cl | 135–136.5 | 15.5 | Benzene-Ethyl acetate-Hexane | C, 54.31<br>H, 5.71<br>N, 11.87 | 54.46<br>5.86<br>11.75 |
| CH$_3$ | OCH$_3$ | —CH$_2$—O—C(CH$_3$)$_2$—C≡CH | Cl | 87–88 | 1.0 | Diethyl Ether | C, 51.96<br>H, 5.46<br>N, 11.96 | 51.78<br>5.55<br>11.40 |

EXAMPLE 7

Following the procedure of Example 6 above, but substituting the appropriate chloromethyl ether and ureidophenol for 1,1-dimethyl-2-propynyl chloromethyl ether and 1-(m-hydroxyphenyl)-3-methoxy-3-methylurea, respectively, yields the following compounds:

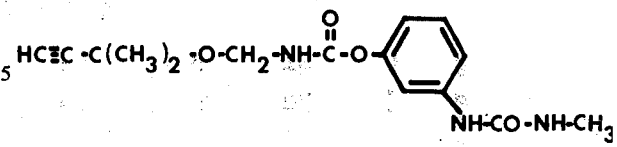

Carbamic acid,
[(1,1-dimethyl-2-propynyloxy)-methyl]-,
m-(3-methylureido)phenyl ester

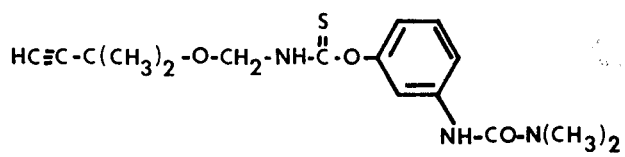

Carbamic acid,
[(1,1-dimethyl-2-propynyloxy)-methyl]-,
m-3-(iso-propylureido)phenyl ester

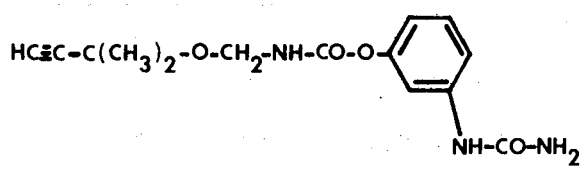

Carbamic acid,
thio[(1,1-dimethyl-2-propynyloxy)-methyl]-,
m-(3,3-dimethylureido)phenyl ester

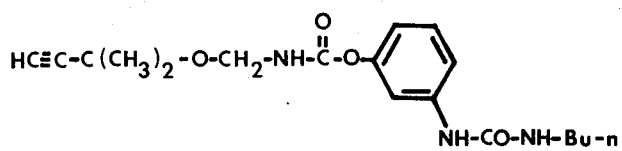

Carbamic acid,
[(1,1-dimethyl-2-propynyloxy)-methyl]-,
m-ureidophenyl ester

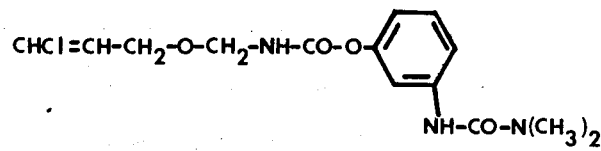

Carbamic acid,
[(1,1-dimethyl-2-propynyloxy)-methyl]-,
m-(3-n-butylureido)phenyl ester Carbamic acid, [(3-chloro-2-allyloxy)methyl],
m-(3,3-dimethylureido)phenyl ester

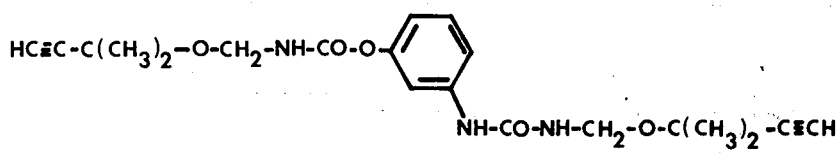

Carbamic acid,
[(1,1-dimethyl-2-propynyloxy)methyl]-m-3-(1,1-dimethyl-2-propynyloxymethylureido)-, phenyl ester Carbamic acid, [(2-chloro-2-allyloxy)methyl]-,
m-(3,3-dimethylureido)phenyl ester

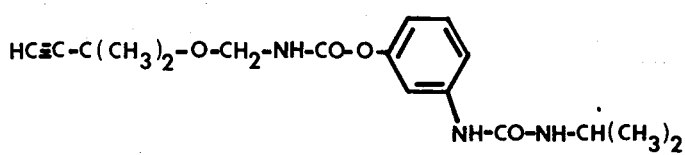

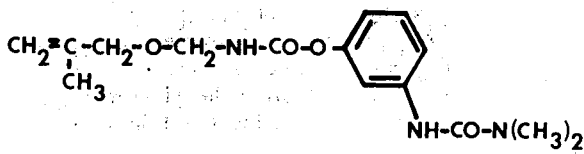

Carbamic acid, [(2-methallyloxy)methyl]-,
m-(3,3-dimethylureido)phenyl ester

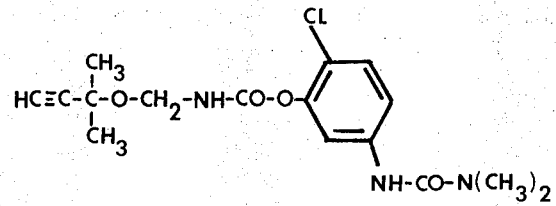

Carbamic acid,
[(1,1-dimethyl-2-propynyloxy)-methyl]-,
2-chloro-5-(3,3-dimethylureido)-phenyl ester

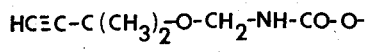

Carbamic acid,
[(1,1-dimethyl-2-propynyloxy)-methyl]-,
2-bromo-5-(3,3-dimethylureido)-phenyl ester

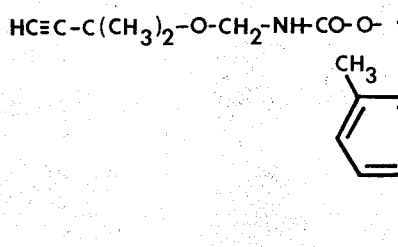

Carbamic acid,
[(1,1-dimethyl-2-propynyloxy)-methyl]-,
2-methyl-5-(3,3-dimethylureido)-phenyl ester

EXAMPLE 8

Preparation of m-(3-Methoxy-3-methylureido)phenyl [(1,1-dimethyl-2-propynyloxy)methyl]carbamate The isocyanate ether solution above (38 ml., 0.015 mole) is added with constant stirring at room temperature (23°C.) to a dry tetrahydrofuran solution (20 ml.) of 1-(m-hydroxyphenyl)-3-methoxy-3-methylurea (2.94 grams, 0.015 mole) containing quinoline (15 ml.), and the reaction stirred overnight at room temperature. A tar separates. The reaction mixture is decanted away from the tar and evaporated to an oil in a crystallizing dish. This oil is treated with 20% HCl (v/v) until the solution is acidic, and then extracted with $CH_2Cl_2$. The methylene chloride layer is then washed with water (100 ml.), washed with a NaOH solution (1% w/v, 100 ml.), water washed, separated, dried over anhydrous $CaCl_2$, filtered, and evaporated to a solution which is crystallized from benzene-hexane to give 0.37 grams of product with a melting point identical to material prepared using triethylamine as base.

EXAMPLE 9

The postemergence herbicidal activity of the compounds of the invention is demonstrated by the following tests, wherein a variety of monocotyledonous and dicotyledonous plants are treated with test compounds dispersed in aqueous acetone mixtures. In the tests, seedling plants are grown in 2 inch square plastic pots for about 2 weeks. The test compounds are dispersed in 50/50 acetone/water mixtures containing 0.5% v/v surfactant in sufficient quantity to provide the equivalent of about 0.06 pound to 4 pounds per acre of active compound when applied to the plants through a spray nozzle operating at 40 psi. for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table V below where it can be seen that the preferred compounds are highly effective for the control of undesirable broadleaf weeds and grasses.

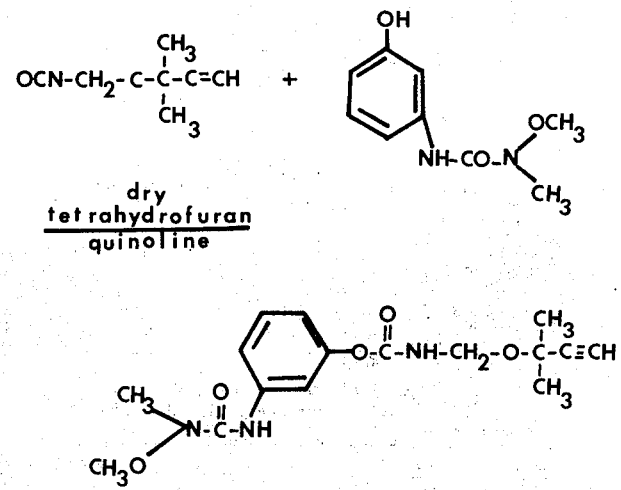

TABLE V

| Compound | Treatment lb./Acre | Postemergence Herbicidal Activity Annual Weeds | | | | | | | | | | | Crops | | |
|---|---|---|---|---|---|---|---|---|---|---|---|---|---|---|---|
| | | LA | MU | PI | RAG | MG | BA | CR | GRF | WO | VE | COR | COT | SOY | R |
| m-(3-methoxy-3-methylureido)phenyl [(1,1-dimethyl-2-propynyloxy)-methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 9 | 9 | 8 | 9 | 9 | 9 | 9 | 7 | 9 | 9 | 9 |
| | 0.13 | 9 | 9 | 9 | 9 | 8 | 3 | 1 | 7 | 1 | 8 | 0 | 9 | 2 | 1 |
| | 0.06 | 3 | 9 | 9 | 0 | 9 | 1 | 1 | 1 | 3 | 7 | 0 | 9 | 5 | 6 |
| m-(3,3-dimethylureido)phenyl [(allyloxy)methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 5 | 9 | 7 | 6 | 6 | 7 | 8 | 1 | 8 | 7 | 7 |
| | 0.13 | 8 | 9 | 7 | 5 | 8 | 5 | 3 | 2 | 2 | 5 | 0 | 8 | 5 | 6 |
| | 0.06 | 5 | 6 | 5 | 3 | 5 | 1 | 0 | 0 | 0 | 0 | 0 | 7 | 5 | 3 |
| m-(3-methoxy-3-methylureido)phenyl [(allyloxy)methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 9 | 9 | 6 | 6 | 6 | 7 | 8 | 3 | 9 | 8 | 7 |
| | 0.13 | 9 | 9 | 9 | 7 | 8 | 3 | 5 | 3 | 5 | 7 | 0 | 9 | 7 | 5 |
| | 0.06 | 6 | 9 | 5 | 2 | 7 | 0 | 0 | 0 | 0 | 0 | 0 | 8 | 5 | 3 |
| m-(3,3-dimethylureido)phenyl [(2-propynyloxy)methyl]carbamate | 1.00 | 9 | 9 | 9 | 9 | 9 | 9 | 9 | 9 | 9 | 9 | 9 | 9 | 9 | 9 |
| | 0.25 | 7 | 9 | 9 | 5 | 7 | 6 | 2 | 3 | 6 | 8 | 0 | 7 | 7 | 6 |
| | 0.13 | 5 | 8 | 9 | 3 | 7 | 5 | 1 | 1 | 2 | 3 | 0 | 7 | 7 | 6 |
| | 0.06 | 2 | 7 | 3 | 1 | 7 | 1 | 1 | 0 | 0 | 0 | 0 | 6 | 5 | 3 |
| m-(3,3-dimethylureido)phenyl [(1-methyl-2-propynyloxy)methyl]carbamate | 1.00 | 9 | 9 | 9 | 9 | 9 | 9 | 9 | 9 | 9 | 9 | 9 | 9 | 9 | 9 |
| | 0.25 | 7 | 9 | 9 | 9 | 8 | 9 | 8 | 8 | 8 | 9 | 3 | 8 | 9 | 8 |
| | 0.13 | 7 | 9 | 9 | 5 | 9 | 3 | 2 | 3 | 3 | 6 | 0 | 8 | 7 | 6 |
| | 0.06 | 5 | 9 | 9 | 3 | 6 | 1 | 1 | 0 | 0 | 1 | 0 | 6 | 5 | 2 |
| m-(3,3-dimethylureido)phenyl [(1,1-dimethyl-2-propynyloxy)methyl]carbamate | 1.00 | 9 | 9 | 9 | 9 | 9 | 9 | 9 | 9 | 8 | 9 | 7 | 9 | 9 | 9 |
| | 0.25 | 9 | 9 | 9 | 9 | 9 | 7 | 8 | 7 | 3 | 9 | 1 | 9 | 8 | 6 |
| | 0.13 | 9 | 9 | 9 | 9 | 9 | 2 | 3 | 3 | 1 | 9 | 0 | 9 | 8 | 5 |
| | 0.06 | 3 | 8 | 9 | 8 | 9 | 0 | 0 | 1 | 0 | 1 | 0 | 9 | 8 | 5 |
| m-(3-methoxy-3-methylureido)phenyl [(2-propynyloxy)methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 8 | 9 | 7 | 7 | 8 | 7 | 9 | 2 | 9 | 8 | 7 |
| | 0.13 | 8 | 9 | 6 | 5 | 8 | 2 | 2 | 3 | 3 | 6 | 0 | 7 | 6 | 5 |
| | 0.06 | 3 | 3 | 2 | 2 | 7 | 0 | 0 | 0 | 0 | 0 | 0 | 6 | 6 | 0 |
| m-(3-methoxy-3-methylureido)phenyl [(1-methyl-2-propynyloxy)methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 9 | 9 | 8 | 8 | 9 | 8 | 9 | 7 | 9 | 9 | 6 |
| | 0.13 | 6 | 9 | 8 | 8 | 9 | 2 | 3 | 6 | 5 | 9 | 2 | 8 | 6 | 5 |
| | 0.06 | 3 | 9 | 6 | 2 | 8 | 0 | 1 | 3 | 0 | 6 | 0 | 7 | 8 | 3 |
| 2-chloro-4-(3,3-dimethylureido)phenyl [(1,1-dimethyl-2-propynyloxy)methyl]carbamate | 4.00 | 9 | 9 | 9 | 9 | 9 | 9 | 9 | 9 | 8 | 9 | 9 | 9 | 9 | 8 |
| | 2.00 | 8 | 9 | 9 | 9 | 9 | 7 | 8 | 9 | 7 | 9 | 7 | 9 | 6 | 7 |
| | 1.00 | 5 | 9 | 7 | 8 | 9 | 5 | 7 | 7 | 1 | 9 | 2 | 9 | 2 | 5 |
| | 0.50 | 2 | 5 | 2 | 2 | 9 | 3 | 3 | 3 | 1 | 1 | 1 | 9 | 2 | 2 |
| m-(3-methoxy-3-methylureido)phenyl [1-(2-propynyloxy)ethyl]carbamate | 4.00 | 9 | 9 | 9 | 9 | 9 | 7 | 7 | 9 | 9 | 9 | 7 | 9 | 9 | 8 |
| | 1.00 | 9 | 9 | 9 | 9 | 9 | 2 | 1 | 8 | 7 | 9 | 1 | 7 | 9 | 2 |
| | 0.25 | 9 | 9 | 9 | 7 | 7 | 0 | 0 | 1 | 0 | 9 | 0 | 2 | 9 | 0 |
| | 0.13 | 8 | 9 | 9 | 1 | 3 | 0 | 0 | 0 | 0 | 3 | 0 | 2 | 2 | 0 |
| 2-chloro-4-(3-methoxy-3-methylureido)phenyl [(1,1-dimethyl-2-propynyloxy)methyl]carbamate | 4.00 | 9 | 9 | 9 | 9 | 9 | 3 | 6 | 8 | 9 | 9 | 5 | 9 | 9 | 8 |
| | 1.00 | 9 | 9 | 9 | 7 | 5 | 0 | 2 | 2 | 2 | 8 | 1 | 7 | 5 | 1 |
| | 0.50 | 8 | 9 | 8 | 1 | 5 | 0 | 0 | 1 | 0 | 1 | 1 | 3 | 3 | 0 |
| | 0.25 | 2 | 9 | 8 | 0 | 0 | 0 | 0 | 0 | 0 | 0 | 0 | 2 | 3 | 0 |
| m-(3-methoxy-3-methylureido)phenyl [1-(1-methyl-2-propynyloxy)ethyl]carbamate | 1.00 | 9 | 9 | 9 | 9 | 9 | 2 | 2 | 9 | 8 | 9 | 6 | 9 | 9 | 7 |
| | 0.25 | 9 | 9 | 9 | 9 | 8 | 0 | 0 | 3 | 3 | 9 | 1 | 7 | 9 | 1 |
| | 0.13 | 9 | 9 | 9 | 7 | 5 | 0 | 0 | 2 | 1 | 9 | 0 | 7 | 5 | 0 |
| | 0.06 | 9 | 9 | 9 | 1 | 5 | 0 | 0 | 0 | 0 | 7 | 0 | 3 | 5 | 0 |
| m-(3-methoxy-3-methylureido)phenyl [1-(1,1-dimethyl-2-propynyloxy)ethyl]carbamate | 4.00 | 9 | 9 | 9 | 9 | 7 | 3 | 7 | 8 | 7 | 9 | 7 | 9 | 9 | 3 |
| | 1.00 | 9 | 9 | 9 | 9 | 7 | 1 | 1 | 2 | 6 | 9 | 0 | 5 | 9 | 1 |
| | 0.25 | 9 | 9 | 9 | 1 | 5 | 0 | 0 | 1 | 1 | 9 | 0 | 5 | 8 | 0 |
| | 0.13 | 9 | 5 | 8 | 1 | 1 | 0 | 0 | 0 | 0 | 7 | 0 | 3 | 7 | 0 |

| Plant Abbreviations | |
|---|---|
| LA | Lambsquarters |
| MU | Mustard |
| PI | Pigweed |
| BA | Barnyard grass |
| CR | Crab grass |
| GRF | Green foxtail |
| WO | Wild oats |
| COR | Corn |
| COT | Cotton |
| SOY | Soybean |
| RAG | Ragweed |
| MG | Morning-glory |
| R | Rice |
| VE | Velvet leaf |

| Rating System: | | % Reduction in Growth as compared to Check* |
|---|---|---|
| 0 | no effect | 0 |
| 1 | possible effect | 1–10 |
| 2 | slight effect | 11–25 |
| 3 | moderate effect | 26–40 |
| 5 | definite injury | 41–60 |
| 6 | herbicidal effect | 61–75 |
| 7 | good herbicidal effect | 76–90 |
| 8 | approaching complete kill | 91–99 |
| 9 | complete kill | 100 |
| 4 | abnormal growth, i.e. a definite physiological malformation but with an over-all effect less than a 5 on the rating scale. | |

*Based on visual determination of stand, size, vigor, chlorosis, growth malformation and over-all plant appearance.

EXAMPLE 10

The preemergence herbicial activity of the compounds of the invention is exemplified by the following tests in which the seeds of a variety of monocotyledonous and dicotyledonous plants are separately mixed with potting soil and planted on top of approximately one inch of soil in separate 2 inch square plastic pots. After planting, the pots are sprayed with the selected aqueous acetone solution containing test compound in sufficient quantity to provide the equivalent of about 0.13 pound to 4 pounds per acre of test compound per pot. The treated pots are then placed on greenhouse benches and cared for an accordance with greenhouse procedures. Three weeks after treatment, the tests are terminated and each pot is examined and rated according to the rating system set forth in the preceding example. The results of these tests establish the herbicidal proficiency of the test compounds for controlling a variety of undesirable plant species.

We claim:

1. A method for the control of undesirable plant species, comprising applying to the foliage of the plants or to the soil containing seeds of the undesirable plants, a herbicidally effective amount of a compund having the formula:

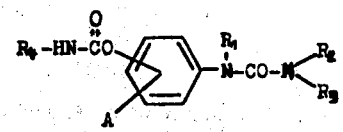

wherein $R_1$ is hydrogen, hydroxyl or alkyl $C_1$–$C_4$; $R_2$ is hydrogen, alkyl $C_1$–$C_4$ or alkoxy $C_1$–$C_4$; $R_3$ is hydrogen, alkyl $C_1$–$C_4$, alkoxy $C_1$–$C_4$,

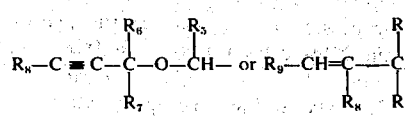 ; $R_4$ is 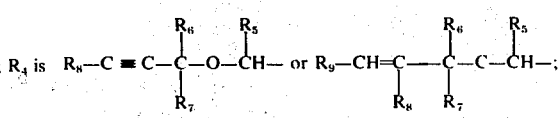

TABLE VI

| Compound | Treatment lb./Acre | Preemergence Herbicidal Activity Annual Weeds |||||||||| Crops |||
|---|---|---|---|---|---|---|---|---|---|---|---|---|---|---|
| | | LA | MU | PI | RAG | MG | BA | CR | GRF | WO | VE | COR | COT | SOY | R |
| m-(3-methoxy-3-methylureido)phenyl [(1,1-dimethyl-2-propynyloxy)methyl]carbamate | 1.00 | 9 | 9 | 9 | 9 | 9 | 9 | 9 | 9 | 9 | 9 | 7 | 9 | 9 | 9 |
| | 0.25 | 9 | 9 | 9 | 9 | 9 | 9 | 9 | 9 | 9 | 9 | 8 | 9 | 8 | 9 |
| | 0.13 | 9 | 9 | 9 | 8 | 9 | 8 | 9 | 8 | 6 | 9 | 8 | 9 | 7 | 7 |
| | 0.06 | 8 | 9 | 9 | 0 | 6 | 1 | 0 | 2 | 1 | 1 | 0 | 0 | 0 | 2 |
| m-(3,3-dimethylureido)phenyl [(allyloxy)methyl]carbamate | 1.00 | 9 | 9 | 9 | 5 | 9 | 3 | 3 | 9 | 9 | 9 | 5 | 9 | 9 | 6 |
| | 0.25 | 7 | 9 | 9 | 2 | 9 | 3 | 3 | 3 | 5 | 9 | 2 | 9 | 3 | 5 |
| | 0.13 | 3 | 9 | 5 | 0 | 0 | 0 | 0 | 0 | 0 | 5 | 0 | 2 | 0 | 5 |
| m-(3-methoxy-3-methylureido)phenyl [(allyloxy)methyl]carbamate | 1.00 | 9 | 9 | 9 | 9 | 9 | 5 | 8 | 8 | 9 | 9 | 5 | 9 | 9 | 7 |
| | 0.25 | 8 | 9 | 9 | 7 | 9 | 2 | 6 | 6 | 7 | 9 | 2 | 9 | 5 | 6 |
| | 0.13 | 5 | 9 | 9 | 0 | 2 | 0 | 0 | 0 | 0 | 8 | 0 | 2 | 0 | 3 |
| m-(3,3-dimethylureido)phenyl [(2-propynyloxy)methyl]carbamate | 1.00 | 8 | 9 | 9 | 8 | 9 | 8 | 9 | 9 | 9 | 9 | 6 | 9 | 9 | 6 |
| | 0.25 | 6 | 9 | 9 | 0 | 9 | 5 | 7 | 3 | 6 | 9 | 0 | 8 | 3 | 5 |
| | 0.13 | 6 | 8 | 9 | 0 | 1 | 3 | 0 | 0 | 1 | 7 | 0 | 0 | 0 | 5 |
| m-(3,3-dimethylureido)phenyl [(1-methyl-2-propynyloxy)methyl]carbamate | 1.00 | 9 | 9 | 9 | 9 | 9 | 9 | 9 | 9 | 9 | 9 | 9 | 9 | 9 | 8 |
| | 0.25 | 7 | 9 | 9 | 7 | 9 | 7 | 8 | 7 | 8 | 9 | 3 | 9 | 8 | 6 |
| | 0.13 | 3 | 9 | 7 | 0 | 6 | 3 | 0 | 0 | 1 | 9 | 0 | 3 | 0 | 3 |
| m-(3,3-dimethylureido)phenyl [(1,1-dimethyl-2-propynyloxy)methyl]carbamate | 1.00 | 9 | 9 | 9 | 9 | 9 | 9 | 9 | 9 | 9 | 9 | 9 | 9 | 9 | 9 |
| | 0.25 | 9 | 9 | 9 | 9 | 9 | 9 | 9 | 9 | 8 | 9 | 9 | 9 | 9 | 8 |
| | 0.13 | 7 | 8 | 8 | 8 | 7 | 9 | 9 | 8 | 5 | 9 | 6 | 9 | 5 | 5 |
| | 0.06 | 3 | 9 | 7 | 5 | 5 | 7 | 8 | 5 | 3 | 7 | 5 | 0 | 0 | 3 |
| m-(3-methoxy-3-methylureido)phenyl [(2-propynyloxy)methyl]carbamate | 1.00 | 9 | 9 | 9 | 9 | 9 | 9 | 9 | 8 | 9 | 9 | 9 | 9 | 9 | 9 |
| | 0.25 | 9 | 9 | 9 | 5 | 9 | 3 | 7 | 6 | 7 | 9 | 2 | 8 | 8 | 5 |
| | 0.13 | 7 | 9 | 8 | 0 | 7 | 1 | 3 | 3 | 1 | 9 | 0 | 3 | 2 | 3 |
| m-(3-methoxy-3-methylureido)phenyl [(1-methyl-2-propynyloxy)methyl]carbamate | 1.00 | 9 | 9 | 9 | 9 | 9 | 9 | 9 | 9 | 9 | 9 | 9 | 9 | 9 | 7 |
| | 0.25 | 8 | 9 | 9 | 8 | 9 | 7 | 9 | 6 | 9 | 9 | 7 | 9 | 9 | 6 |
| | 0.13 | 8 | 9 | 9 | 5 | 9 | 6 | 2 | 3 | 6 | 9 | 3 | 3 | 0 | 5 |
| 2-chloro-4-(3,3-dimethylureido)phenyl [(1,1-dimethyl-2-propynyloxy)methyl]carbamate | 2.00 | 8 | 9 | 9 | 5 | 9 | 3 | 0 | 0 | 0 | 9 | 0 | 9 | 3 | 3 |
| | 1.00 | 7 | 9 | 7 | 2 | 5 | 0 | 0 | 0 | 0 | 7 | 0 | 3 | 0 | 1 |
| | 0.50 | 3 | 3 | 3 | 0 | 0 | 0 | 0 | 0 | 0 | 0 | 0 | 0 | 0 | 0 |
| m-(3-methoxy-3-methylureido)phenyl [1-(2-propynyloxy)ethyl]carbamate | 4.00 | 9 | 9 | 8 | 7 | 9 | 7 | 7 | 6 | 7 | 8 | 0 | 8 | 9 | 5 |
| | 1.00 | 5 | 5 | 2 | 5 | 8 | 0 | 0 | 0 | 1 | 2 | 0 | 0 | 0 | 2 |
| | 0.50 | 2 | 0 | 0 | 0 | 2 | 0 | 0 | 0 | 0 | 0 | 0 | 0 | 0 | 0 |
| 2-chloro-4-(3-methoxy-3-methylureido)phenyl [(1,1-dimethyl-2-propynyloxy)methyl]carbamate | 4.00 | 9 | 9 | 9 | 9 | 9 | 8 | 9 | 8 | 6 | 9 | 5 | 6 | 7 | 5 |
| | 1.00 | 9 | 9 | 8 | 8 | 5 | 2 | 5 | 2 | 1 | 9 | 0 | 0 | 0 | 1 |
| | 0.50 | 7 | 3 | 0 | 2 | 7 | 0 | 0 | 0 | 0 | 6 | 0 | — | 0 | 0 |
| m-(3-methoxy-3-methylureido)phenyl [1-(1-methyl-2-propynyloxy)ethyl]carbamate | 4.00 | 9 | 9 | 8 | 7 | 9 | 7 | 7 | 6 | 6 | 9 | 0 | 9 | 6 | 5 |
| | 1.00 | 8 | 5 | 0 | 0 | 0 | 0 | 0 | 0 | 1 | 1 | 0 | 0 | 1 | 1 |
| | 0.50 | 3 | 0 | 0 | 0 | 0 | 0 | 0 | 0 | 0 | 0 | 0 | 0 | 0 | 0 |
| m-(3-methoxy-3-methylureido)phenyl [1-(1,1-dimethyl-2-propynyloxy)ethyl]carbamate | 4.00 | 8 | 9 | 8 | 2 | 9 | 5 | 5 | 5 | 2 | 9 | 0 | 5 | 5 | 3 |
| | 1.00 | 7 | 6 | 6 | 3 | 5 | 0 | 0 | 3 | 1 | 2 | 0 | 0 | 0 | 1 |
| | 0.50 | 0 | 0 | 0 | 0 | 0 | 0 | 0 | 0 | 1 | 0 | 0 | 0 | 0 | 0 |

$R_5$ is hydrogen or n-alkyl $C_1$–$C_4$; $R_6$ and $R_7$ are hydrogen or alkyl $C_1$–$C_4$; $R_8$ and $R_9$ are hydrogen, alkyl $C_1$–$C_4$ or halogen; and A is hydrogen, ahlogen or alkyl $C_1$–$C_4$; provided that A and —O—CO—NHR$_4$ are meta- and para-, respectively, or para- or meta-, respectively; and provided that $R_2$ is hydrogen when $R_3$ is either

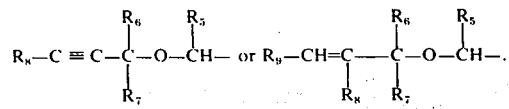

2. A method according to claim 1, wherein the compound is applied at the rate of from 0.06 pound to 8 pounds per acre.

3. A method according to claim 1, wherein $R_1$ is hydrogen; $R_2$ is methyl or methoxy; $R_3$ is methyl; A is hydrogen;

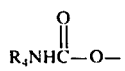

is meta- to the ureido group; $R_4$, $R_6$, $R_7$, $R_8$ and $R_9$ are as defined in claim 1, and $R_5$ is hydrogen.

4. A method according to claim 3 wherein the compound applied is m-(3-methoxy-3-methylureido)phenyl [(1,1-dimethyl-2-propynyloxy)methyl]carbamate.

5. A method according to claim 3, wherein the compound applied is m-(3,3-dimethylureido)phenyl [(1,1-dimethyl-2-propynyloxy)methyl]carbamate.

6. A method according to claim 3 wherein the compound applied is m-(3,3-dimethylureido)phenyl [(allyloxy)-methyl]carbamate.

7. A method according to claim 3 wherein the compound applied is m-(3,3-dimethylureido)phenyl [(2-propynyloxy)methyl]carbamate.

8. A method according to claim 3 wherein the compound applied is m-(3,3-dimethylureido)phenyl [(1-methyl-2-propynyloxy)methyl]carbamate.

9. A method for the postemergence control of undesirable plant species according to claim 1, comprising applying the compound to the foliage of the undesirable plant species at the rate of from 0.06 pound to 1 pounds per acre.

10. A method for the preemergence control of undesirable plant species according to claim 1, wherein the compound is applied at the rate of from 0.06 pound to 8 pounds per acre to soil containing seeds of the undesirable plants.

11. A method according to claim 1 for the selective postemergence control of undesirable plant species, comprising applying the compound to the foliage of the undesirable plant species in the presence of an agronomic crop at the rate of from 0.06 pound to 2 pounds per acre.

12. A method according to claim 1 for the selective preemergence control of undesirable plant species, comprising applying the compound to soil containing seeds of the undesirable plants and seeds of an agronomic crop at a rate of between about 0.06 pound and 6 pounds per acre.

* * * * *